United States Patent [19]
Markantes et al.

[11] Patent Number: 5,596,402
[45] Date of Patent: Jan. 21, 1997

[54] VIEWING DEVICE AND METHOD FOR ASCERTAINING SIMULTANEOUSLY OPTICAL COLOR SHIFT CHARACTERISTICS OF AN OPTICALLY VARIABLE DEVICE

[75] Inventors: Charles T. Markantes; Roger W. Phillips, both of Santa Rosa, Calif.

[73] Assignee: Flex Products, Inc., Santa Rosa, Calif.

[21] Appl. No.: 607,919

[22] Filed: Feb. 28, 1996

Related U.S. Application Data

[63] Continuation of Ser. No. 330,902, Oct. 27, 1994, abandoned.
[51] Int. Cl.⁶ ............................. G06K 9/74; B42D 15/00; G02B 27/22; G01N 21/25
[52] U.S. Cl. .................... 356/71; 356/420; 359/2; 359/471; 359/472; 359/475; 359/477; 283/91; 283/85; 283/57; 428/913; 428/915; 428/916
[58] Field of Search ................... 356/71, 420; 428/913, 428/916; 283/91, 94, 85, 86, 57, 59, 114, 902–903; 359/2, 32, 471–472, 475, 477

[56] References Cited

U.S. PATENT DOCUMENTS

| | | | |
|---|---|---|---|
| 3,744,917 | 7/1973 | Craig | 356/71 |
| 4,618,257 | 10/1986 | Bayne et al. | 356/71 |
| 4,968,064 | 11/1990 | Mancuso | 356/71 |

*Primary Examiner*—Frank Gonzalez
*Assistant Examiner*—Jason D. Eisenberg
*Attorney, Agent, or Firm*—Flehr, Hohbach, Test, Albritton & Herbert

[57] ABSTRACT

A viewing device for use by an observer to ascertain the authenticity of an instrument of value having an image formed from an optically variable device. The viewing device includes a frame structure which permits viewing of the image in a fixed spatial orientation and a reflector carried by the frame structure for permitting the observer to see simultaneously the image in first and second colors without movement of the observer, the viewing device or the image.

28 Claims, 4 Drawing Sheets

VIEWING DEVICE AND METHOD FOR ASCERTAINING SIMULTANEOUSLY OPTICAL COLOR SHIFT CHARACTERISTICS OF AN OPTICALLY VARIABLE DEVICE

This is a continuation of application Ser. No. 08/330,902 filed Oct. 27, 1994, now abandoned.

BACKGROUND OF THE INVENTION

1. Field of the Invention

This invention pertains generally to viewers or viewing devices and, more particularly, to viewing devices having reflectors therein.

2. Description of the Related Art

Optically variable devices are disclosed in U.S. Pat. Nos. 4,705,300 and 4,705,356. Optically variable devices which can be used in optically variable inks and optically variable pigments are disclosed in U.S. Pat. Nos. 5,171,363 and 5,279,657. The color shift characteristics of these devices and inks can be used for currency authentication. Relative movement between the observer and the optically variable device is typically needed to visualize these color shifts. There is a need for a viewing device which can be used by an observer to confirm the authenticity of an optically variable device without the need of relative movement between the observer, the optically variable device or the viewing device.

In general, it is an object of the present invention to provide a viewing device which permits an observer to quickly confirm the color shift characteristics of an optically variable device.

Another object of the invention is to provide a viewing device of the above character which permits the observer to simultaneously view two discrete colors reflected by an optically variable device.

Another object of the invention is to provide a viewing device of the above character in which the confirmation of authenticity of an optically variable device is reproducible.

Additional objects and features of the invention will appear from the following description from which the preferred embodiments are set forth in detail in conjunction with the accompanying drawings.

SUMMARY OF THE INVENTION

In general, the viewing device of the present invention is for use by an observer to ascertain the authenticity of an instrument of value having an image thereon formed from an optically variable device. The viewing device includes a frame structure which permits viewing of the image in a fixed spatial orientation and means carried by the frame structure for permitting the observer to see simultaneously the image in first and second colors without movement of the observer, the viewing device or the image.

DETAILED DESCRIPTION

More in particular, a viewing device of the present invention is utilized to determine the authenticity of an instrument of value such as a bank note 16 having an image 17 thereon formed from an optically variable device 18 which causes substantial color shifts with varying angle of light incidence. Optically variable device 18 can, for example, be a thin film optically variable article such as that disclosed in U.S. Pat. Nos. 4,705,300 and 4,705,356 or an optically variable printing ink such as that disclosed in U.S. Pat. Nos. 5,171,363 and 5,279,657. As more fully discussed in U.S. Pat. No. 4,705,356, image 17 exhibits a significant change in colored appearance when viewed from two different angles which differ, for example, by at least 40° and up to approximately 70°. A suitable optically variable device 18 exhibits a color shift between green and blue. The angle of reflection of a ray of light from image 17 is generally equal to the angle of incidence of the ray of light illuminating the image.

Figures 1, 2, 3:
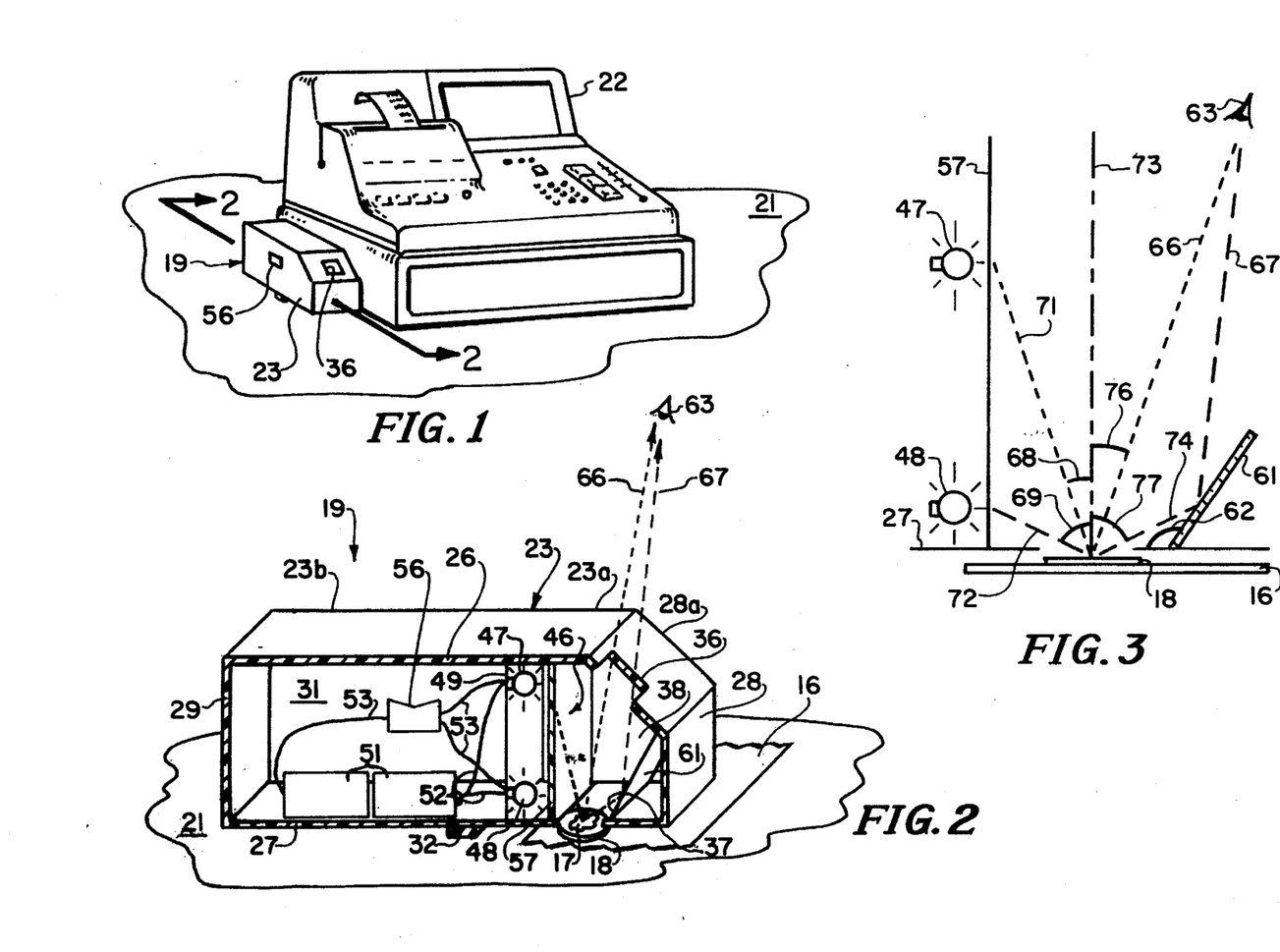
FIG. 1 is a perspective view of a viewing device incorporating the present invention in an operational position relative to a cash register.
FIG. 2 is cross-sectional view of the viewing device of FIG. 1 taken along the line 2—2 of FIG. 1.
FIG. 3 is a diagram illustrating certain relationships of the viewing device of FIG. 1.

A viewer or viewing device 19 of the present invention is utilized at places where currency or other instruments of value are transferred for goods, services or other items of value. In FIG. 1, a viewing device 19 is shown on a support surface 21 next to a cash register 22. Viewing device 19 is formed from a frame structure or housing 23 made from any suitable opaque material such as molded plastic. As illustrated in FIG. 2, housing 23 is generally in the form of a parallelepiped having top and bottom portions 26 and 27, front and rear walls 28 and 29 and first and second side walls 31. Front wall 28 has an upper inclined or bevelled portion 28a which extends inwardly and upwardly to connect with top portion 26. Housing 23 has a length of approximately twelve inches and a height of approximately four and one-half inches.

Housing 23 permits image 17 to be viewed when bank note 16 is in a fixed spacial orientation resting on support surface 21. In this regard, rear portion 23b of the housing is provided with foot 32 for supporting viewing device 19 above the support surface and permitting the bank note to be slid under front portion 23a of the housing. Inclined portion 28a is provided with an upper viewing port 36 and bottom portion 27 of housing 23 is provided with a lower viewing port 37 to permit viewing of image 17 on the bank note through viewing compartment 38 in front portion 23a of the housing.

Housing 28 of viewing device 19 includes means for permitting an observer to view image 17 in a first color and simultaneously view the image in a second color without movement of the observer, the viewing device or the image. In this regard, lighting means in the form of lighting assembly 46 is carried within housing 23 for illuminating image 17 through lower viewing port 37 and permitting the observer to view the image through ports 36 and 37 in a first color. Lighting assembly 46 includes at least one light emanating source and, more specifically as shown in FIG. 2, includes a first or upper light or bulb 47 and a second or lower light or bulb 48 spaced below bulb 47. Bulbs 47 and 48 are mounted on a reflector panel 49 extending between top and bottom portions 26 and 27 and side walls 31 in general vertical disposition. The bulbs can be of a suitable size such as 0.3A and 2.5V for producing illumination on the sample surface of optically variable device 18 ranging from approximately 25 to 100 footcandles. Housing 23 is provided with an internal power supply in the form of first and second batteries 51 which are electrically connected to bulbs 47 and 48 by first wires 52 for providing electrical energy to the bulbs. Second wires 53 serve as a ground return between the bulbs and batteries 51 and a switch 56 is mounted to one of side walls 31 and electrically connected to second wires 53 for energizing and de-energizing the bulbs.

A translucent planar diffuser sheet 57 made from any suitable material such as plastic and having a thickness of approximately 0.1 millimeter is vertically mounted within housing 23 adjacent and rearwardly of viewing port 37 as part of lighting assembly 46. Diffuser sheet 57 extends between top and bottom portions 26 and 27 and sidewalls 31 of housing 23 and thus defines the rear wall of viewing compartment 38. Sheet 57 diffuses the light entering the viewing compartment from bulbs 47 and 48. It should be appreciated that a diffuser sheet which is curved in conformation and/or mounted at an oblique angle relative to image 17 would be within the scope of the present invention.

Reflector means in the form of a generally planar mirror 61 is included within viewing device 19 for permitting the observer to simultaneously view image 17 in a second color. Mirror 61 is located forward of lower viewing port 37 opposite diffuser sheet 57 and is mounted in viewing compartment 38 so as to extend at an oblique angle from bottom portion 27 of housing 23 to front wall 28. More specifically, mirror 61 intersects bottom portion 27 a distance from the center of image 17 ranging from approximately zero to six inches and is aligned at an obtuse angle 62 ranging from approximately 90° to 135° relative to image 17 in the horizontal plane and preferably at an angle ranging from approximately 110° to 120°. Although mirror 61 is shown as being generally planar, it could be curved and be within the scope of the present invention.

The relative relationship of bulbs 47 and 48, diffuser sheet 57 and mirror 61 are important in the operation of viewing device 19 and are illustrated in FIG. 3 relative to the plane below viewing device 19 containing image 17 of optically variable device 18 and relative to an observer indicated by eye 63. These components of viewing device 19 are placed so that first reflected ray 66 containing the view of image 17 in the first desired color intersects second reflected ray 67 containing the view of the image in the second desired color at the proper location relative to viewing device 19 for facilitating ease of observation by eye 63. In this regard, it has been found that a suitable point of intersection of rays 66 and 67 is approximately 30 inches from an image 17 which is placed beneath lower viewing port 37 in housing 23.

The horizontal distance from the center of image 17 to diffuser sheet 57 and the vertical distance between the plane of the image and upper and lower bulbs 47 and 48 determines first and second relative angles of illumination or incidence 68 and 69 of respective first and second incident rays 71 and 72 emanating from bulbs 47 and 48. Angles of incidence 68 and 69, measured relative to a plane which is normal to optically variable device 18 and is shown in FIG. 3 by line 73, range from approximately 15° to 40° and 60° to 85°, respectively, and approximate 35° and 80° respectively, in the embodiment illustrated in FIGS. 1 and 2. First incident ray 71 produces first reflected ray 66 and second incident ray 72 produces reflected ray 74 which, when reflected by mirror 61, in turn produces second reflected ray 67. The mirror causes second color reflected ray 67 to intersect first color reflected ray 66 generally at eye 63.

First color reflected ray 66 and reflected ray 74 have respective first and second angles of reflection 76 and 77 which are equal to first and second angles of incidence 68 and 69. As such, angles of reflection 76 and 77 define the respective first and second viewing angles of rays 66 and 67 perceived by eye 63. It is desirable that the angle of separation between reflected rays 66 and 74 be at least 40° and most desirably range from approximately 40° to 70°. Thus, rays 66 and 67 contain the colors reflected from image 17 at angles 76 and 77.

In operation and use, viewing device 19 and the method thereof permits an observer to ascertain the optical color shift characteristics of optically variable device 18 and to thereby verify the authenticity of bank note 16. After the bank note is slipped under front portion 23a of housing 23 so that image 17 is generally aligned with lower viewing port 37, light switch 56 is activated so that upper and lower bulbs 47 and 48 illuminate the image through the lower viewing port. The opaque material of housing 23 and the small size of upper viewing port 36 minimizes the amount of ambient light reaching the image. As such, bulbs 47 and 48 provide two relatively discrete sources of light for illuminating the image at respective angles of incidence 68 and 69.

First incidence ray 71 from upper bulb 47 illuminates optically variable device 18 at first angle of incidence 68 so as to reflect or project image 17 in the first color at reflection angle 76 directly through upper viewing port 36 to the observer. Second incident ray 72 from lower bulb 48 illuminates device 18 at second angle of incidence 69 and causes second reflected ray 74 to project the image in the second color at reflection angle 77 onto mirror 61 mounted in housing 23 at an oblique angle relative to the image. The colored image of second reflected ray 67 is reflected by the mirror through upper viewing port 36 and, as seen by the observer, is a reverse of the image of first reflected ray 66. In this manner, viewing device 19 permits the observer to view the color shift characteristics of image 17 to a general fixed line of sight.

The relative placement of bulbs 47 and 48 and diffuser sheet 57 causes the difference between angles 77 and 76 of reflected rays 66 and 67 to be in the desired range of at least 40° for ensuring an optimal and discernable color shift between the image as projected by first and second color reflected rays 66 and 67. The visualization of the color shift characteristics of optically variable device 18 enables the observer to confirm the authenticity of bank note 16.

Although the discussion above has referred to individual incident rays 71 and 72 and reflected rays 66 and 67, it will be appreciated by those skilled in the art that diffuser sheet 57 serves to convert each of bulbs 47 and 48 from a single light source to a plurality of light sources which generally decrease in intensity from the point on the diffuser sheet closest to the respective bulb. Each of these light sources of lesser intensity illuminates the image at a discrete angle of incidence and produces a reflected ray which projects the image at a discrete angle of reflection. The angular diversity of these various reflected images provides a plurality of viewing points at which the observer can see image 17 in both of the desired colors so as to confirm authenticity.

Viewing device 19 provides a quick and repeatable means for confirming the optical color shift characteristics of image 17. The viewing device does not rely upon ambient light, the direction and intensity of which can change over time, to illuminate optically variable device 18. Instead, the viewing device provides lighting from bulbs 47 and 48 which is relatively constant in color profile, illumination and direction. In addition, the viewing angles are defined by the location of viewing ports 36 and 37 and are relatively constant. Accordingly, the authenticity of the same or similar bank notes can be repeatedly confirmed as necessary.

Figures 4, 5, 6:
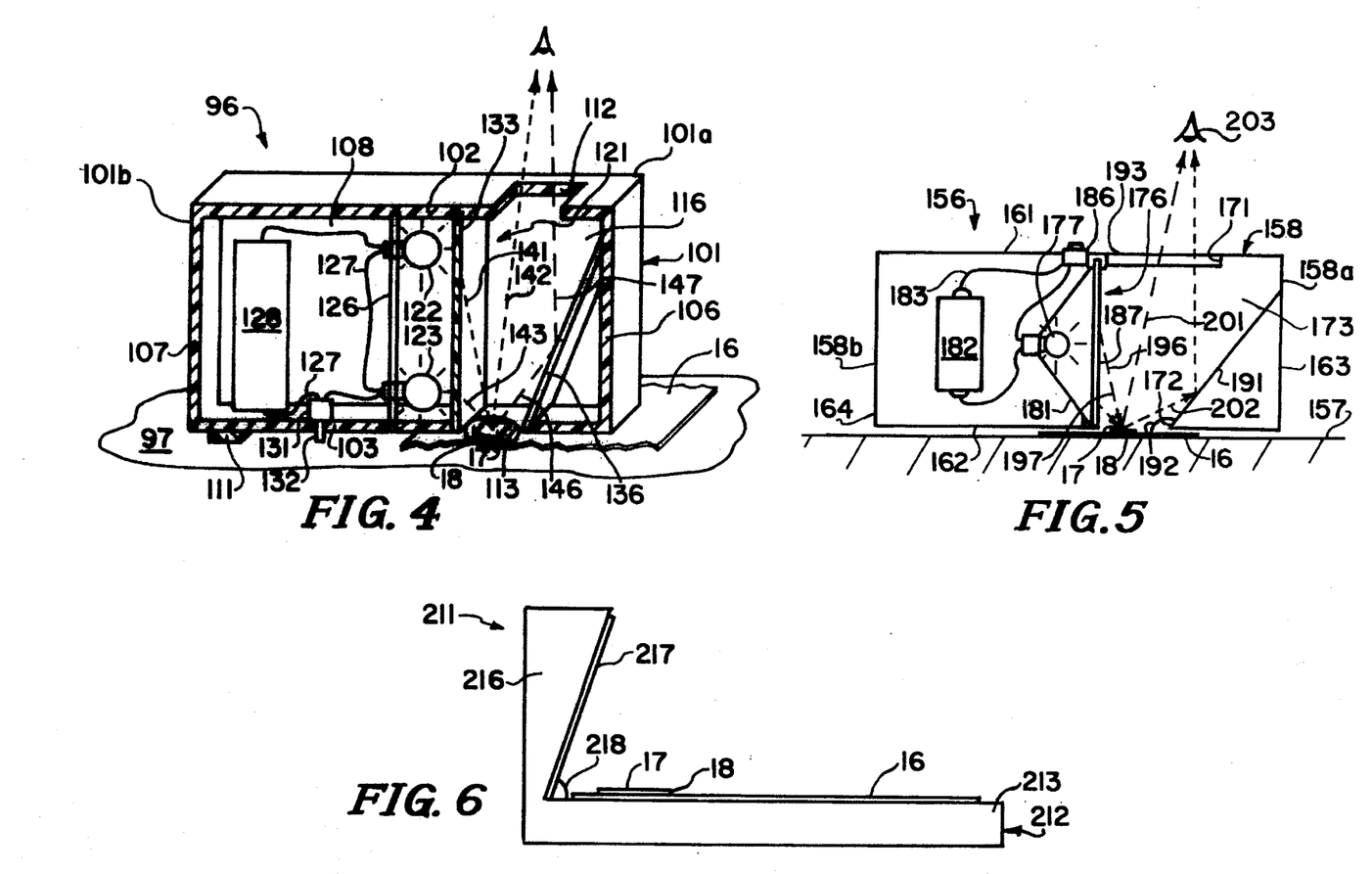
FIG. 4 is a cross sectional view, somewhat schematic, of another embodiment of a viewing device incorporating the present invention.
FIG. 5 is a cross sectional view, somewhat schematic, of another embodiment of a viewing device incorporating the present invention.
FIG. 6 is a side elevational view, somewhat schematic, of another embodiment of a viewing device incorporating the present invention.

A viewing device having first and second internally fixed light sources can have other embodiments and be within the scope of the present invention. A compact viewing device 96 having features similar to viewing device 19 is illustrated in FIG. 4. Viewing device 96 is for use on a support surface 97 and includes a housing 101 made from any suitable opaque material such as molded plastic. Housing 101 is generally in the form of a parallelepiped and has top and bottom portions 102 and 103, front and rear walls 106 and 107 and first and second side walls 108. The housing is provided with front and rear portions 101a and 101b. Rear portion 101b is provided with a foot 111. Upper and lower viewing ports 112 and 113 are provided in housing front portion 101a to permit the bank note to be viewed through viewing compartment 116 of the housing front portion.

Viewing device 96 includes an internal lighting means or assembly 121 for illuminating image 17 through lower viewing port 113. Lighting assembly 121 includes first and second vertically-spaced light sources in the form of first or upper conventional bulb 122 and second or lower conventional bulb 123 mounted in a generally planar reflector plate 126 extending between top and bottom portions 102 and 103 and side walls 108 in general vertical disposition near the center of housing 101. Bulbs 122 and 123 are electrically connected by wires 127 to a power supply in the form of battery 128 which is mounted within rear portion 101b of the housing. Wires 127 are connected to an on/off switch 131 which is mounted to bottom portion 103 of housing 101 and includes a spring-loaded plunger 132 that activates the switch and extends downwardly from bottom portion 103 so as to engage support surface 97. A generally planar sheet 133 made from any suitable translucent material such as plastic is mounted forward of bulbs 122 and 123 and rearward of ports 112 and 113 and serves to diffuse the light emanating from the bulbs in a manner discussed above.

A reflector means in the form of mirror 136 is mounted at an oblique angle relative to bottom portion 103 in viewing compartment 116. More specifically, mirror 136 is disposed forward of ports 112 and 113 and extends transversely between side walls 108 and upwardly and forwardly from bottom portion 103 toward front wall 106.

Bulbs 122 and 123, diffuser sheet 133 and mirror 136 are mounted in viewer housing 101 in a manner similar to bulbs 47 and 48, diffuser sheet 57 and mirror 61 of viewing device 19. Briefly, upper bulb 122 and diffuser sheet 133 produce first incident light 141 and corresponding first reflected ray 142 which projects image 17 in a first color to the observer. Lower bulb 123 and diffuser sheet 133 produce second incident light 143 and corresponding reflected light 146 which is reflected by mirror 136 to project the image in a second color via second reflected ray 147 to the observer for simultaneous visualization with the image of first reflected ray 142.

In operation and use, viewing device 96 is lifted and placed on bank note 16 so that image 17 is beneath front portion 101a in general alignment with lower viewing port 113 and visible through front portion 101a of housing 101. Viewing device 96 is pressed downwardly by the observer so as to pivot about foot 111 and depress plunger 132 until the front lower edge of front portion 101a engages support surface 97. The depressed plunger actuates switch 131 and causes bulbs 122 and 123 to be energized and illuminate the image through diffuser sheet 133. First and second reflected rays 142 and 147 are projected to a point which allows the observer to simultaneously view the image in the first and second colors and thereby ascertain the authenticity of bank note 16.

A further embodiment of the present invention having internal lighting is illustrated in FIG. 5. Viewing device 156 therein is for use on a support surface 157 and is similar in many respects to viewing device 96. The viewing device includes a housing 158 made from any suitable opaque material such as plastic. Housing 158 has upper and lower portions 161 and 162 and front and rear walls 163 and 164 and is provided with front and rear portions 158a and 158b. Upper and lower ports 171 and 172 are respectively formed in upper and lower portions 161 and 162 of the housing to permit the observer to see through viewing compartment 173 within front portion 158a of the housing. Housing 158 has a length of approximately five and one-half inches and a height and width of approximate two and one-half inches.

A lighting means or assembly 176 is included within viewing device 156 and includes a single lighting source or bulb 177 mounted at the apex of a generally conical reflector 181 which extends between upper and lower portions 161 and 162 so as to face forwardly toward viewing compartment 173. A battery 182 is mounted within rear portion 158b of the housing and serves as a power supply for energizing bulb 177. Wires 183 electrically connect the battery to the bulb and are also connected to an on/off switch 186 mounted to upper portion 161. A generally planar sheet 187 of any suitable translucent material such as plastic is mounted to the front of reflector 181 for serving as a diffuser.

Reflector means in the form of mirror 191 is mounted within viewing compartment 173 forward of ports 171 and 172 and extends at an oblique angle 192 from lower portion 162 toward front wall 163. Magnifying means in the form of a plastic lens 193 is mounted within upper viewing port 171 so as to magnify images viewed therethrough and preferably has a magnification ratio of 2:1.

In operation and use, viewing device 156 is placed on support surface 157 over a bank note 16 so that image 17 is visible through lower viewing port 172. Switch 186 is activated so that bulb 177 emanates light for illuminating the image of the bank note. As noted above, diffuser sheet 187 serves to diffuse the light from bulb 177 so as to produce a plurality of light sources on the diffuser sheet. Incident light from each light source illuminates the image of the bank note from a different angle. This incident light includes at least first and second incident rays 196 and 197 which illuminate image 17 at respective first and second angles of illumination or incidence (not shown). First and second incident rays respectively produce first and second reflected rays 201 and 202 which project the image in the first and second colors at respective first and second angles of reflection (not shown) to the observer, indicated by eye 203 in FIG. 5. Mirror 191 alters the direction of second reflected ray 202 so that the observer can simultaneously see image 17 in the first and second colors without movement of eye 203, viewing device 156 or bank note 16. Magnifying lens 193 serves to enlarge the projected images so as to enhance to the observer any detail in the image.

The viewing devices of the present invention can utilize ambient light to ascertain the color shift characteristics of optically variable devices. For example, viewing device 211 shown in side elevational plan in FIG. 6 and schematically in FIGS. 7 and 8 has means for permitting an observer to see image 17 simultaneously in first and second colors without movement of the observer, the viewing device or the image. Viewing device 211 includes a frame structure or frame 212 having a generally horizontal platform 213 adapted for receiving bank note 16 and having a length of at least four inches. An upstanding portion 216 extends upwardly in a general vertical direction from the rear of platform 213 and is formed integral with the platform. A reflector means or reflector in the form of mirror 217 is carried by frame 212 at an angle relative to image 17 and extends a distance of at least four inches upwardly from and over the rear of the platform. More specifically, mirror 217 is mounted to upstanding portion 216 at an angle 218 ranging from 50° to 90°, preferably from 60° to 80° and more preferably approximately 70° relative to platform 213.

Figures 7, 8, 9:
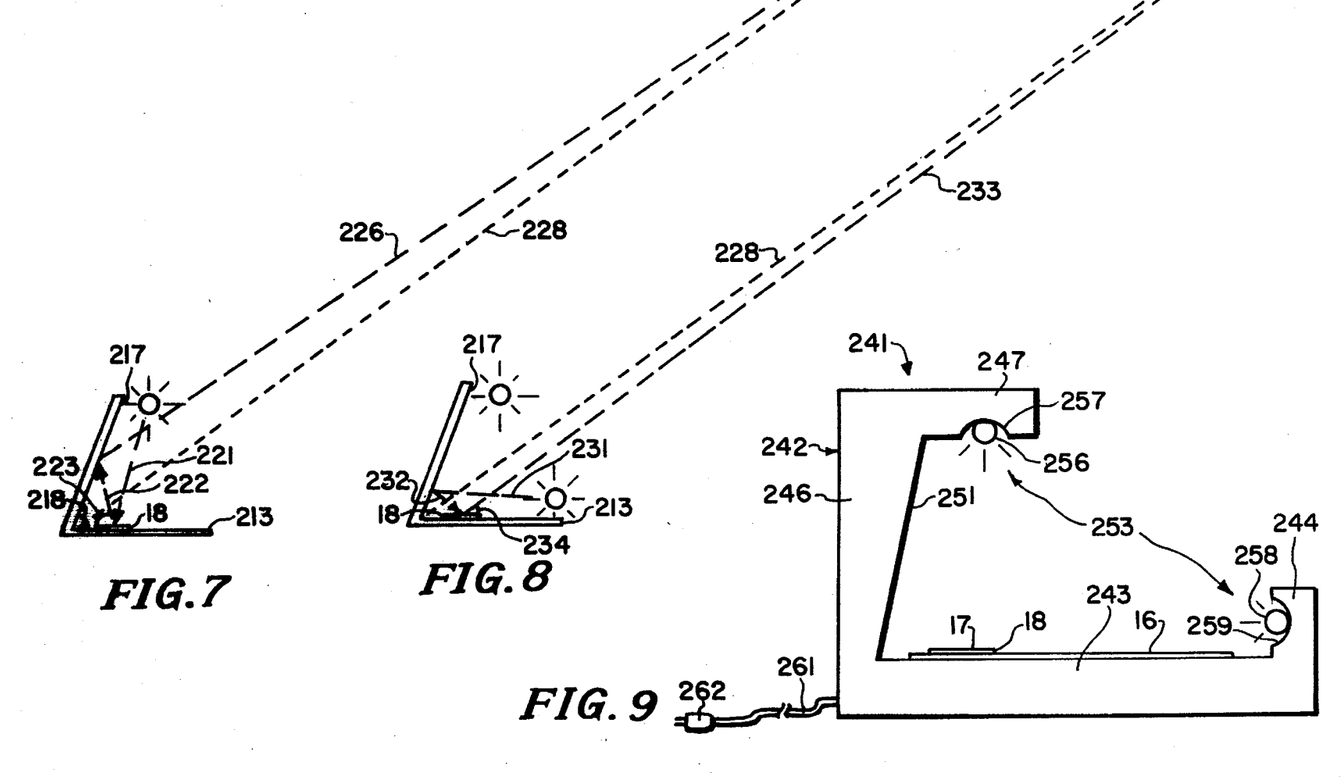
FIG. 7 is a diagram illustrating certain relationships of the viewing device of FIG. 6.
FIG. 8 is a diagram illustrating certain other relationships of the viewing device of FIG. 6.
FIG. 9 is a side elevational view, somewhat schematic, of another embodiment of a viewing device incorporating the present invention.

In operation and use, ambient light, illustrated in part by a first ambient ray 221 in FIG. 7, illuminates image 17 and reflects therefrom at a first angle of reflection 223 to produce reflected ray 222. Mirror 217, which is mounted to frame 213 at an oblique angle relative to image 17, serves to reflect ray 222 at a preferred angle of approximately 37° to produce first reflected ray 226 of image 17. Ray 226 projects the image in a first color into a region about 30 inches from the point of intersection of platform 213 and mirror 217 for observation by the observer indicated by eye 227 in FIGS. 7 and 8. First reflected ray 226 is shown in FIG. 7 relative to a line 228 bisecting mirror angle 218 and extending toward eye 227. A second ambient ray 231, illustrated in FIG. 8, reflects ambient ray 232 from mirror 217 at a preferred angle of approximately 74° onto image 17. Ray 232 reflects from image 17 at a second angle of reflection 234 to produce second reflected ray 233 which projects the image in a second color into the same region and permits the observer to simultaneously view the image in the second color. By way of example, first and second reflection angles 223 and 234 can equal approximately 74° and 37°, respectively, and, as such, rays 226 and 233 are in effect reflected from the image at an effective angle difference of approximately 37°. It should be appreciated that the angles shown in FIGS. 7 and 8 may vary depending on the horizontal positioning of device 18 on platform 213 relative to the base of mirror 251.

A viewer similar to viewing device 211 can be supplemented by light sources and be within the scope of the present invention. In FIG. 9, a viewing device 241 is provided having a frame structure or frame 242 provided with a generally horizontal platform 243 adapted for receiving a bank note 16. A light housing 244 extends upwardly from the front of platform 243. Frame 242 further includes an upstanding portion 246 extending upwardly from the rear of platform 243 and formed integral therewith. A second light housing in the form of overhang 247 extends forwardly in a general horizontal direction from the top of the upstanding portion over platform 243. A reflector means or reflector in the form of mirror 251 extends from the rear of the platform in an upward and forward direction to overhang 247 so as to be disposed at an acute angle of approximately 70° relative to platform 243. Mirror 251 is adhered to upstanding portion 246 by any suitable adhesive (not shown).

Viewing device 241 further includes a lighting means or system 253 which includes a bulb 256 mounted within a generally conical reflector housing 257 at the end of overhang 247. The reflector and bulb are positioned so that light therefrom illuminates platform 243 at approximately 16° from the normal. Bulb 256 is recessed sufficiently into the reflector housing so that no light from the reflector housing or bulb reaches the observer. Lighting system 253 further includes a light bulb 258 and a generally conical reflector housing 259 mounted in light housing 244 such that light therefrom strikes mirror 251 at a slight angle from the horizontal, for example 3°. An electrical cord 261 is electrically connected in series to bulbs 256 and 258 and has a conventional connector 262 at the other end to permit connection of the bulbs to a suitable power supply.

Viewing device 241 operates in substantially the same manner as viewing device 211 except that bulbs 256 and 258, instead of ambient light, serve as light sources. More specifically, bank note 16 with optically variable device 18 is placed on the upper flat surface of platform 243. Directed light from the bulbs reaches image 17 and reflects two different colored images of the optically variable device back toward the observer in the same manner as shown in FIGS. 7 and 8 with respect to viewing device 211. In this manner, image 17 of the optically variable device can be seen via two rays of light similar to rays 230 and 231 in FIGS. 7 and 8.

Figure 10:
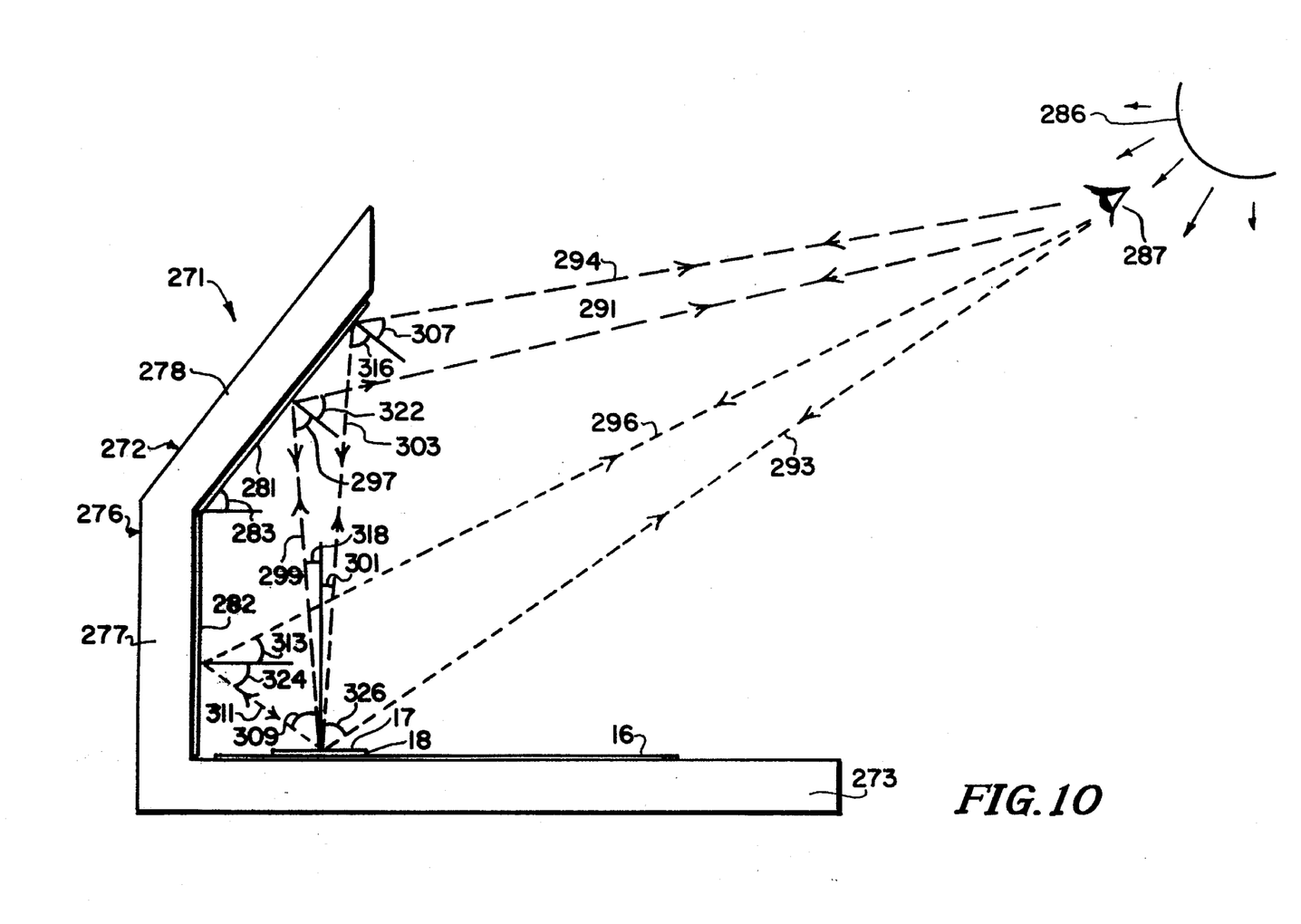
FIG. 10 is a side elevational view, somewhat schematic, of another embodiment of a viewing device incorporating the present invention.

In another embodiment of this invention, which is illustrated in FIG. 10, a viewing device 271 is provided which is integrally formed from a frame structure or frame 272 made from any suitable material such as metal, wood or plastic. Frame 272 is comprised of a horizontally extending platform 273 and a concave reflector means or assembly 276 extending in a general vertical direction from the platform. Reflector assembly 276 includes a generally straight upstanding portion 277 joined at a right angle to platform 273 and a generally straight overhang portion 278 extending upwardly from the top of the upstanding portion and forwardly over the platform. First reflector portion or upper mirror 281 and second reflector portion or lower mirror 282 are secured respectively to the front surfaces or portions 278 and 277 by any suitable adhesive (not shown) so that lower mirror 282 is in general perpendicular alignment relative to platform 273 and upper mirror 281 is at an acute angle 283 of approximately 50° relative to the horizontal. Platform 273 has a horizontal dimension at least equal to the large dimension of a bank note and equally sized mirrors 281 and 282 are generally square with a side dimension ranging from four to six inches.

In the operation of viewing device 271, ambient light is provided by light source 286 positioned behind the observer indicated by eye 287. This light consists of rays 291 and 293 or rays 294 and 296 depending on the position of eye 287. In one position, rays 291 and 293 are incoming ambient rays from light source 286. Ray 291 passes to upper mirror 281 where it reflects at an angle 297 relative to a line normal to the mirror to produce reflected ray 299. The reflected ray 299 passes to image 17 where it reflects off at an angle 301 relative to a line normal to the image back toward mirror 281 as reflected ray 303. The ray 303 is reflected by mirror 281 at an angle 307 relative to the normal of the mirror toward eye 287 as ray 294. Ambient ray 293 strikes image 17 where it reflects off at an angle 309 relative to a line normal to the image to produce reflected ray 311. The reflected ray 311 passes to lower mirror 282 where it reflects off at an angle 313 relative to a line normal to the mirror toward eye 287 as ray 296.

A slight displacement of eye 287 causes rays 294 and 296 to serve as incoming light rays from source 286 and rays 291 and 293 to become reflected rays. In brief, ray 294 reflects from upper mirror 281 at an angle 316 from its normal to produce reflected ray 303, which in turn strikes image 17 and reflects thereof at an angle 318 measured relative to a line normal to the image to produce reflected ray 299. The reflected ray 299 passes back to the upper mirror where it reflects off this mirror at angle 322 toward eye 287 as ray 291. Similarly, ray 296 passes to lower mirror 282 where it reflects at angle 324 relative to a line normal to that mirror to produce reflected ray 311. The ray 311 reflects off image 17 at angle 326 toward eye 287 as ray 293.

In the case of a green-to-blue optically variable device 18, the color blue would be seen in rays 293 or 296 and the color green would be seen in rays 291 or 294. In the corner cube arrangement of viewing device 271, the size of the reflection angles can vary within respective ranges which produce generally the same line of sight from light emanating near eye 287 to light coming back to the eye. In one workable arrangement, reflection angles 309 and 326 are approximately 55° and reflection angles 313 and 324 are approximately 35°. In this arrangement, reflection angles 297 and 322 and 307 and 316 are approximately 50° and reflection angles 301 and 318 range from approximately 3° to 6° —the size of reflection angles 301 and 318 being dependent upon the travel distance of reflected rays 299 and 303 between upper mirror 281 and the plane of image 17. The distance from the observer to the bottom of lower mirror 282 in this arrangement ranges from approximately 18 to 24 inches.

Although the viewing devices of the present invention have been shown relative to optically variable device 18 with certain illustrated and described incident and reflecting rays having related angles of incidence and reflection, it should be appreciated that device 18 can be otherwise positioned relative to the viewing devices to permit simultaneous viewing of image 17 in the first and second colors and be within the scope of the present invention. In addition, viewing devices having one or two mirrors positioned at angles relative to device 18 other than as shown herein can also be provided and be within the scope of the present invention.

From the foregoing, it can be seen that a viewing device has been provided which permits an observer to quickly confirm the color shift characteristics of an optically variable device by simultaneously viewing two discrete colors reflected by the optically variable device. The confirmation of authenticity of the optically variable device is reproducible by the viewing device.

What is claimed is:

1. A viewing device for use by an observer to view a local area of a pattern of an instrument of value, the pattern formed from a generally planar optically variable device using optical interference technology and having optical color shift characteristics so as to reflect a first color when viewed at a first viewing angle and a second color when viewed at a second viewing angle relative to a light source, comprising a viewing structure adapted for ascertaining that the instrument of value is authentic, the viewing structure permitting the observer to view the local area of the pattern formed from the optically variable device in a fixed spatial orientation, and means carried by the viewing structure for permitting the observer to see the local area of the pattern formed from the optically variable device simultaneously in juxtaposed first and second colors without movement of the observer, the viewing device or the pattern, said means including a reflector carried by the viewing structure and disposed at an angle relative to the pattern for reflecting the second color from the local area of the pattern to the observer.

2. A viewing device as in claim 1 wherein the reflector is disposed at an acute angle relative to the pattern.

3. A viewing device as in claim 1 wherein the reflector is disposed at an angle ranging from 50° to 90° relative to the pattern.

4. A viewing device as in claim 1 wherein the reflector is disposed at an angle ranging from 60° to 80° relative to the pattern.

5. A viewing device as in claim 1 wherein the reflector is disposed at an obtuse angle relative to the pattern.

6. A viewing device as in claim 1 wherein the reflector is disposed at an angle ranging from 90° to 135° relative to the pattern.

7. A viewing device as in claim 1 wherein the pattern lies in a plane and wherein the reflector includes a first reflector portion disposed at an acute-angle relative to the plane of the pattern for reflecting the first color from the local area of the pattern to the observer and a second reflector portion extending between the first reflector portion and the plane of the pattern at a substantially right angle relative to the plane of the pattern for reflecting the second color from the local area of the pattern to the observer.

8. A viewing device as in claim 7 wherein the acute angle is approximately 50°.

9. A viewing device as in claim 1 wherein said means includes at least one source of light carried by the viewing structure which emanates light for illuminating the local area of the pattern.

10. A viewing device as in claim 9 further comprising means carried by the viewing structure for diffusing the light from the at least one source of light.

11. A viewing device as in claim 9 further comprising a power supply carried by the viewing structure and electrically connected to the at least one source of light for providing electrical energy to the same.

12. A viewing device for use by an observer to view a local area of a pattern of an instrument of value, the pattern formed from an ink having an optically variable pigment with optical color shift characteristics so as to reflect a first color when viewed at a first viewing angle and a second color when viewed at a second viewing angle relative to a light source, comprising a support structure adapted to permit viewing of the local area of the pattern formed from the optically variable pigment in a fixed spatial orientation, lighting means carried by the support structure for illuminating the local area of the pattern formed from the optically variable pigment to permit the observer to view said local area in the first color at the first viewing angle, and a reflector disposed at an oblique angle relative to the pattern to permit the observer to view the local area of the pattern formed from the optically variable pigment as reflected by the reflector in the second color at the second viewing angle, the lighting means and reflector included within means carried by the support structure for permitting an observer to perceive simultaneously the optical color shift characteristics of the optically variable pigment and thus verify that the instrument of value is authentic.

13. A viewing device as in claim 12 wherein the difference between the first and second viewing angles defines a separation angle and wherein the lighting means is included with means for causing a separation angle of at least 40°.

14. A viewing device as in claim 13 wherein the lighting means is included with means for causing a separation angle ranging from approximately 40° to 70°.

15. A viewing device as in claim 13 wherein the lighting means includes a source of light and a diffuser carried by the support structure between the source of light and the pattern.

16. A viewing device as in claim 13 wherein the lighting means includes first and second spaced-apart sources of light.

17. A method for authenticating an instrument of value having a pattern formed from a generally planar optically variable device using interference technology and having optical color shift characteristics so as to reflect a first color when viewed at a first viewing angle and a second color when viewed at a second viewing angle, comprising projecting the pattern in the first color at the first viewing angle into a region and projecting the pattern in the second color at the second viewing angle into the region so that the pattern can be viewed simultaneously in the region in the first and second colors and the instrument of value verified as authentic.

18. The method of claim 17 further comprising illuminating the pattern at a first illumination angle.

19. The method of claim 18 further comprising simultaneously illuminating the pattern at a second illumination angle.

20. An authenticity checking device for use by a human eye of an observer with an instrument of value having an optically variable device using optical interference technology on at least a portion thereof, said optically variable device being planar and providing a color shift between a first color at a first angle of incidence relative to the optically variable device and a second color at a second angle of incidence relative to the optically variable device, comprising a housing having a viewing port therein into which the instrument of value can be positioned with the optically variable device being disposed in the viewing port, at least one source of light providing light rays which impinge upon the optically variable device of the instrument of value, a reflector disposed within the housing and reflecting at least one color so that the two colors are visually displayed in a relationship for being viewed simultaneously in a side by side manner by the human eye of the observer without movement of the human eye whereby when the two colors are viewed simultaneously the observer can ascertain that the instrument of value is authentic.

21. An authenticity checking device as in claim 20 wherein said at least one source of light is ambient light.

22. An authenticity checking device as in claim 20 wherein said at least one source of light is disposed within the housing.

23. An authenticity checking device as in claim 20 wherein said at least one source of light is first and second spaced-apart light sources.

24. An authenticity checking device as in claim 23 wherein the first and second spaced-apart light sources have intensities which are the same so that the two colors have the same intensity.

25. An authenticity checking device as in claim 23 further including a diffuser through which the light rays pass before impinging upon the optically variable device so as to prevent images of the first and second spaced-apart light sources appearing in the colors being viewed by the observer.

26. An authenticity checking device as in claim 20 wherein the optically variable device includes a pattern.

27. A viewing device for use by an observer to view a local area of a pattern of an instrument of value, the pattern formed from a generally planar optically variable device using interference technology and having optical color shift characteristics so as to reflect a first color when viewed at a first viewing angle and a second color when viewed at a second viewing angle relative to a light source, comprising a housing having a viewing port through which the local area of the pattern formed from the optically variable device can be viewed in a fixed spatial orientation, first and second spaced-apart sources of light carried within the housing for illuminating the local area of the pattern formed from the optically variable device and a reflector carried within the housing and disposed at an oblique angle relative to the pattern, the first source of light permitting the observer to view the local area of the pattern through the viewing port in the first color at the first viewing angle and the second source of light and the reflector permitting the observer to view the local area of the pattern through the viewing port in the second color at the second viewing angle so that the observer can perceive simultaneously the optical color shift characteristics of the optically variable device and thus verify that the instrument of value is authentic.

28. A viewing device as in claim 27 further including a diffuser carried within the housing between the first and second sources of light and the viewing port for preventing images of the sources of light from appearing in the colors being viewed by the observer.

* * * * *